(12) United States Patent
Midmore

(10) Patent No.: US 9,672,466 B2
(45) Date of Patent: *Jun. 6, 2017

(54) METHODS AND SYSTEMS OF FOUR-VALUED GENOMIC SEQUENCING AND MACROMOLECULAR ANALYSIS

(71) Applicant: Roger Midmore, San Francisco, CA (US)

(72) Inventor: Roger Midmore, San Francisco, CA (US)

( * ) Notice: Subject to any disclaimer, the term of this patent is extended or adjusted under 35 U.S.C. 154(b) by 254 days.

This patent is subject to a terminal disclaimer.

(21) Appl. No.: 14/095,416

(22) Filed: Dec. 3, 2013

(65) Prior Publication Data

US 2015/0066835 A1   Mar. 5, 2015

Related U.S. Application Data

(63) Continuation-in-part of application No. 14/016,518, filed on Sep. 3, 2013, now Pat. No. 9,576,244, and a continuation-in-part of application No. 14/016,538, filed on Sep. 3, 2013, now Pat. No. 9,575,951, and a continuation-in-part of application No. 14/051,722, filed on Oct. 11, 2013, now Pat. No. 9,576,319.

(51) Int. Cl.
*G06N 5/04* (2006.01)
*G06N 5/02* (2006.01)
*G06F 19/22* (2011.01)

(52) U.S. Cl.
CPC ............. *G06N 5/02* (2013.01); *G06F 19/22* (2013.01); *G06N 5/04* (2013.01)

(58) Field of Classification Search
None
See application file for complete search history.

(56) References Cited

U.S. PATENT DOCUMENTS

| | | | |
|---|---|---|---|
| 8,977,953 B1* | 3/2015 | Pierre et al. | 715/230 |
| 2005/0282193 A1* | 12/2005 | Bulyk et al. | 435/6 |
| 2008/0221892 A1* | 9/2008 | Nathan et al. | 704/257 |
| 2011/0119047 A1* | 5/2011 | Ylonen | 704/9 |

OTHER PUBLICATIONS

"Algorithms for Paraconsistent Reasoning with OWL", Yue Ma, Pascal Hitzler, Zuoquan Lin, The Semantic Web: Research and Applications, Lecture Notes in Computer Science, vol. 4519, 2007, pp. 399-413.*

"High Performance Natural Language Processing on Semantic Network Array Processor", Hiroaki Kitano, Dan Moldovan, Seungho Cha, IJCAI, vol. 12, No. 1991, pp. 911-917, 1991.*

(Continued)

*Primary Examiner* — Alan Chen
*Assistant Examiner* — Mai T Tran
(74) *Attorney, Agent, or Firm* — West & Associates, A PC; Stuart West

(57) ABSTRACT

A four-valued logic system for genomic sequencing and macromolecular analysis using a semantic network having object nodes and relationships between the object nodes. The object nodes are each represented by two vectors with true, false, defined, or undefined values in corresponding bits in the two vectors. Conditionals or quantifying variables are tested during successive recursive steps in a predicate calculus using the four-valued logic system.

13 Claims, 9 Drawing Sheets

Diagram of the arrays (with size = N) associated with each Semantic Node

(56) References Cited

OTHER PUBLICATIONS

"An Overview of Rewrite Rule Laboratory (RRL)", Deepak Kapur, Hantao Zhang, Rewriting Techniques and Applications, Lecture Notes in Computer Science, vol. 355, 1989, pp. 559-563.*
Semantic Network Array Processor as a Massivley Paralllel Computing Platform for High Performance and Large-Scale Natural Language Processing, H. Kitano, D. Moldovan, COLING '92 Proceedings of the 14th conference on Computational linguistics, Nantes, Aug. 23-28, 1992, vol. 2 , pp. 813-819.*
Englemore, R. and Tony Morgan, (1988). Blackboard Systems. New York. Addisson Wesley Publishers.
Halton, J., (1968). "A Retrospective and Prospective Survey Of The Monte Carlo Method". University of Wisconin Computer Science Tech Report #13. Feb. 1968.
Hays, David, Bozena Henisz-Dostert and Marjorie Rapp (editor). (1965) "Annotated Bibliography of Rand Publications in Computational Linguistics". Rand Memorandum RM-3894-3.
Hays, David. Marjorie Rapp and Boana Henisz-Dostert & Jean Houston (editors). (1965) "Bibliography of Computational Linguitics 1964". Rand Memorandum RM-4523-PR March.
Hays, David. Marjorie Rapp and Boana Henisz-Dostert & Jean Houston (editors). (1966) "Bibliography of Computational Linguistics 1965". Rand Memorandum 4986-PR. April.
Hays, David. Marjorie Rapp, Boana Henisz-Dostert & Jean Houston (editors). (1967) "Bibliography of Computational Linguistics 1966". Rand Memorandum RM-5345-PR. April.
Hays, David. Boana Henisz-Dostert & Jean Houston (editors). (1968). "Bibliography of Computational Linguistics 1967". Rand Memorandum RM-5733-PR. July.
Hays,D, Henisz-Dostert, Bozena. Jean Houston & Dolores Lofgren (editors). (1970). "Bibliography of Computational Linguistics 1968". Rand Memorandum RM-6233-PR. January.
Herdan, G. (1966). The Advanced Theory of Language as Choice or Chance. Spring-Verlag.
Kleene, S., (1951) "Representation Of Events In Nerve Nets And Finite Automata". Rand Memorandum RM-704. December.
Kleene, S. , (1952). Introduction to Metamathematics. North Holland.
Kleene, S. and Richard Vesley, (1965). The Foundations Of Intuitionistic Mathematics Especially In Relation To Recursive Functions. North-Holland.
Kleene, S., (1967). Mathematical Logic. John Wiley. New York.
Kleene, S., (1973)."Realizability: A Retrospective Survey". Cambridge Summer School in Mathematical Logic. Edited by Mathias, R. and H. Rogers. p. 95-112.
Kleene,S., (1981). "The Theory of Recursive Functions, Approaching Its Centennial". Bulletin of the American Mathematical Society. vol. 5, No. 1, Jul. 1981.
Klein, S. and Robert Simmons, (1963). "A Computational Approach to the Grammatical Encoding of English Words". Journal for the Association for Computing Machinery. vol. 10 N. 3 July.
Klein, S. and Robert Simmons. (1963). "Syntactic Dependence and the Computer Generation of Coherent Discourse". Mechanical Translation, vol. 7 No. 2, August.
Klein, S. (1965). "Automatic Paraphrasing In Essay Format". Mechanical Translation, vol. 8 N. 3&4, Aug.-Dec. 1965.
Klein, S. (1965). "Control of Style With A Generative Grammar". Lanugage 41: 619-631.
Klein, S. (1966). "Historical Change in Language Using Monte Carlo Techniques". Mechanical Translation. 9: 619-631.
Klein, S., Stephen Lieman and Gary Lindstrom, (1966). "DISEMINER: A Distributional Semantics Inference Maker". Carnegie Mellon University Tech Report #1719.
Klein, S. (1967). "Current Research in the Computer Simulation of Historical Change in Language". University of Wisconsin Tech Report #6. Aug. 1967.
Klein, S. W. Febens, R. Herriot, W. Katke, M. Kupping & A. Towster. (1968). "The AUTOLING System". Univeristy of Wisconsin Tech Report #43, Sep. 1968.

Klein, S., M. Kuppins and K. Meives. (1969). "Monte Carlo Simulation of Language Change in Tikopia and Maori". University of Wisconsin Tech Report #62. Jun. 1969.
Klein, S. and Michael Kuppin (1970). "An Interactive, Heuristic Program for Learning Transformational Grammars". Univeristy of Wisconsin Tech Report #97. Aug. 1970.
Klein, S., Oakley J., Surballe D. and Robert Ziesmer (1971). "A Program for Generating Reports on the Status and History of Stochastically Modifiable Semantic Models of Arbitrary Universes". University of Wisconsin Tech Report #142. Nov. 1971.
Klein, S. and T. Dennison. (1971). "An Interactive Program for Learning the Morphology of Natural Languages". University of Wisconsin Tech Report #144. Dec. 1971.
Klein, S. (1973). "Automatic Inference of Semantic Deep Structure Rules in Generative Semantic Grammars." University of Wisconsin Tech Report #180. May 1973.
Klein, S., J. Aeschlimann, D. Balsiger, S. Converse, C. Court, M. Foster, R. Lao, J. Oakley and J. Smith. (1973). "Automatic Novel Writing: A Status Report" University of Wisconsin Technical Report #186. Dec. 1973.
Klein, S and V. Rozencevj (1974). "A Computer Model for the Ontogeny of Pidgin and Creole Languages". University of Wisconsin Tech Report #238. Dec. 1974.
Klein, S. (1974). "Computer Simulation of Language Contact Models". Toward Tomorrow's Linguistics. Edited by R. Shuy & C. J. Bailey. Georgetown University Press, 1974. pp. 276-290.
Klein, S. (1975). "Meta-Compiling Text Grammars as a Model for Human Behavior". University of Wisconsin Tech Report #252. Apr. 1975.
Klein, S., John Aeschlimann, Matthew Appelbaum, David Balsiger, Elizabeth Curtis, Mark Foster, David Kalish, Ying-Da Lee and Lynee Price.,(1976). "Forward: The History of MESSY". University of Wisconsin Technical Report #272.
Klein, S., D. Kaufer and Christine Neuwirth. (1979). "The Locus Of Metaphor In Frame Driven Text Grammar". University of Wisconsin Tech Report #366. Sep. 1979.
Klein, S.. (1981). "Culture, Mysticism and Social Structure and the Calculation of Behavior". University of Wisconsin Technical Report #462.
Klein, S. (1983). "Analogy, Mysticism and the Structure of Culture". Current Anthropology. vol. 24 N. 2. Apr. 1983.
Klein, S. (1985). "The Invention of Computationally Plausible Knowledge Systems in the Upper Paleolithic". University of Wisconsin Tech Report #628. Dec. 1985.
Klein, S. (2002). "The Analogical Foundations of Creativity in Language, Culture & the Arts: the Upper Paleolithic to 2100 CE". Language, Vision & Music, edited by Paul McKevitt, Mulvihill & Nuallin. John Benjamin, pp. 347-371.
Lukasiewicz, J. (1955). Aristotle's Syllogistic From the Standpoint of Modern Formal Logic. 2nd edition. Oxford.
Siemens, D. (1988). "On Klein's 'Analogy, Mysticism and the Structure of Cultre'". Current Anthropology, vol. 29 No. 3. Jun. 1988.
Steedman, M.,(1992). "Categorial Grammar". University of Pennsylvania Department of Computer and Information Science Technical Report No. MS-CIS-92-52.
Troelstra, A.S., (1999)."From Constructivism to Computer Science". Theoretical Computer Science, No. 211, 1999 p. 233-252.
Turing, Alan, (1947). "Lecture To The London Mathematical Society on Feb. 20, 1947". Unpublished Manuscript. In Alan Turing: His work and Impact. Edited by S. Cooper and Jan Leeuwen. 2012.
Turing, Alan, (1954). "Solvable and Unsolvable Problems". Science News, No. 31, p. 7-23.
Yngve , V.,(1996). From Grammar to Science: New Foundations for General Linguistics. Amsterdam.
Belnap, N., Leblanc H. & R. Thomason. "On Not Strengthening Intuitionistic Logic". Notre Dame Journal of Formal Logic vol. 4 No. 4, Oct. 1963.
Chretien, D. (1965). "Review of The Calculus of Linguistic Observations". Language vol. 4 No. 2, 1965.
Midmore, R,. (2014). "An Interpretation of Sheldon Klein's Four Valued Analogical Transformationl Operator". University of Wisconsin Technical Report #1801. Feb. 2014.

(56) References Cited

OTHER PUBLICATIONS

Kleene S."Representation Of Events In Nerve Nets And Finite Automata". Rand Memorandum RM-704. USA. Dec. 1951.
Kleene S. Introduction to Metamathematics. North Holland. USA. 1952. pp. 207, 317-337, 382, 536.
Kleene S. and Richard Vesley. The Foundations Of Intuitionistic Mathematics Especially In Relation To Recursive Functions. North-Holland. USA. 1965. pp. 133-163.
Kleene S. Mathematical Logic. John Wiley. New York. 1967. pp. 176, 240-241.
Kleene S."Realizability: A Retrospective Survey". Cambridge Summer School in Mathematical Logic. Edited by Mathias, R. and H. Rogers. p. 95-112. 1973. p. 104.
Kleene S. "The Theory of Recursive Functions, Approaching Its Centennial". Bulletin of the American Mathematical Society. vol. 5, No. 1. USA. Jul. 1981. pp. 57-61.
Klein S. and Robert Simmons. "A Computational Approach to the Grammatical Encoding of English Words". Journal for the Association for Computing Machinery. vol. 10 N. 3. USA.
Klein S. and Robert Simmons. "Syntactic Dependence and the Computer Generation of Coherent Discourse". Mechanical Translation, vol. 7 No. 2. USA. Aug. 1963.
Klein S. "Automatic Paraphrasing In Essay Format". Mechanical Translation, vol. 8 N. 3&4. USA. Aug.-Dec. 1965.
Klein S. "Control of Style With A Generative Grammar". Language 41: 619-631. USA. 1965.
Klein S. "Historical Change in Language Using Monte Carlo Techniques". Mechanical Translation. 9: 619-631. USA. 1966.
Klein S., Stephen Lieman and Gary Lindstrom. "DISEMINER: A Distributional Semantics Inference Maker". Carnegie Mellon University Tech Report #1719. USA. 1966.
Klein S. "Current Research in the Computer Simulation of Historical Change in Language". University of Wisconsin Tech Report #6. USA. Aug. 1967.
Klein S., W. Febens, R. Herriott, W. Katke, M. Kupping & A. Towster. "The AUTOLING System". University of Wisconsin Tech Report #43. USA. Sep. 1968.
Klein S., M. Kuppins and K. Meives. "Monte Carlo Simulation of Language Change in Tikopia and Maori". University of Wisconsin Tech Report #62. USA. Jun. 1969.
Klein S. and Michael Kuppin. "An Interactive, Heuristic Program for Learning Transformational Grammars". University of Wisconsin Tech Report #97. USA. Aug. 1970.
Klein S. and T. Dennison. "An Interactive Program for Learning the Morphology of Natural Languages". University of Wisconsin Tech Report #144. USA. Dec. 1971.
Klein S. "Automatic Inference of Semantic Deep Structure Rules in Generative Semantic Grammars." University of Wisconsin Tech Report #180. USA. May 1973.
Klein S. and V. Rozencevj. "A Computer Model for the Ontogeny of Pidgin and Creole Languages". University of Wisconsin Tech Report #238. USA. Dec. 1974.
Klein S. "Computer Simulation of Language Contact Models". Toward Tomorrow's Linguistics. Edited by R. Shuy & C. J. Bailey. Georgetown University Press. USA. 1974.
Klein S. "Meta-Compiling Text Grammars as a Model for Human Behavior". University of Wisconsin Tech Report #252. USA. Apr. 1975.
Klein S., D. Kaufer and C. Neuwirth. "The Locus Of Metaphor In Frame Driven Text Grammar". University of Wisconsin Tech Report #366. USA. Sep. 1979.
Klein S. "Culture, Mysticism and Social Structure and the Calculation of Behavior". University of Wisconsin Technical Report #462. USA. 1981.
Klein S. "Analogy, Mysticism and the Structure of Culture". Current Anthropology. vol. 24 No. 2. USA. Apr. 1983. pp. 156-162.
Klein S. "The Invention of Computationally Plausible Knowledge Systems in the Upper Paleolithic". University of Wisconsin Tech Report #628. USA. Dec. 1985.
Lukasiewicz J. Aristotle's Syllogistic From the Standpoint of Modern Formal Logic. Oxford University Press. England. 1955. 2nd edition. pp. 158-173.
Siemens D. "On Klein's 'Analogy, Mysticism and the Structure of Culture'". Current Anthropology, vol. 29 No. 3. USA. Jun. 1988. pp. 472-478.
Steedman M. "Categorial Grammar". University of Pennsylvania Department of Computer and Information Science Technical Report No. MS-CIS-92-52. USA. 1992.
Troelstra A.S."From Constructivism to Computer Science". Theoretical Computer Science, No. 211, 1999. pp. 236-239.
Turing A. "Solvable and Unsolvable Problems". Alan Turing: His work and Impact. Edited by S. Cooper and Jan Leeuwen. Elsevier Science. United Kingdom. 2012. p. 331.
Yngve V. From Grammar to Science: New Foundations for General Linguistics. John Benjamins Publishing. Amsterdam. 1996. pp. 47-63.
Belnap N., H. Leblanc & R. Thomason. "On Not Strengthening Intuitionistic Logic". Notre Dame Journal of Formal Logic, vol. 4 No. 4. USA. Oct. 1963.
Chretien D. "Review of The Calculus of Linguistic Observations". Language, vol. 4 No. 2. USA. 1965.
Midmore R. "An Interpretation of Sheldon Klein's Four Valued Analogical Transformational Operator". University of Wisconsin Technical Report #1801. USA. Feb. 2014.
Norvig P. and S. Russell. Artificial Intelligence: A Modern Approach. Pearson Education Inc. New Jersey, 2003. pp. 7-8.
Shapiro S. and R. Bechtel. "A Logic for Semantic Networks". University of Indiana Technical Report #47. USA. Mar. 1976.
Reichenbach H. The Theory of Probability. University of California Press. Berkeley and Los Angeles. USA. 1949. pp. xi, 387-401.
Lamport L. "Time, Clocks and the Ordering of Events in a Distributed System". Communications of the ACM. vol. 21 No. 7. USA. 1978.
Searls D. "The Linguistics of DNA". American Scientist, vol. 80 No. 6. USA. Nov.-Dec. 1992. pp. 579-584.
Zhurkin V., N. Ulyanov, A. Gorin and R. Jernigan. "Static and Statistical Bending of DNA Evaluated by Monte Carlo Simulations". Proceedings of the National Academy of Science.
Englemore, R. and Tony Morgan. Blackboard Systems.. Addisson Wesley Publishers. New York. 1988. pp. 475-490.
Halton, J. "A Retrospective and Prospective Survey Of The Monte Carlo Method". University of Wisconsin Computer Science Tech Report #13. Feb. 1968.
Hays D., Marjorie Rapp, Boana Henisz-Dostert & Jean Houston (editors). "Bibliography of Computational Linguitics 1964". Rand Memorandum RM-4523-PR. Mar. 1965. pp. 1-5.
Hays ., Marjorie Rapp, Boana Henisz-Dostert & Jean Houston (editors). "Bibliography of Computational Linguistics 1965". Rand Memorandum 4986-PR. Apr. 1966. pp. 1-5.
Hays D., M, Boana Henisz-Dostert & Jean Houston (editors). "Bibliography of Computational Linguistics 1966". Rand Memorandum RM-5345-PR. Apr. 1967. pp. 1-5.
Hays D., Boana Henisz-Dostert & Jean Houston (editors). "Bibliography of Computational Linguistics 1967". Rand Memorandum RM-5733-PR. Jul. 1968. pp. 1-5.
Hays D, Boana Henisz-Dostert, Jean Houston & Dolores Lofgren (editors). "Bibliography of Computational Linguistics 1968". Rand Memorandum RM-6233-PR. Jan. 1970. pp. 1-5.
Herdan G. The Advanced Theory of Language as Choice or Chance. Spring-Verlag. The Hague 1966. pp. 438-445.
Norvig, P. and Stuart Russell. (2003). Artificial Intelligence: A Modern Approach. Pearson Education Inc. New Jersey, 2003.
Shapiro, S. and Robert Bechtel. (1976). "A Logic for Semantic Networks". University of Indiana Technical Report #47. Mar. 1976.
Meini, C. and A. Paternoster. (1996). "Understanding Language Through Vision". Artificial Intelligence Review 10: 37-48.
Wachsmuth, I, B. Lenzmann, T. Jording, B. Jung M. Latoschik and Martin Frohlich. (1997). "A Virtual Interface Agent and It's Agency". Proceedings of the First International Conference on Autonomous Agents. 1997.
Searls, D., "The Linguistics of DNA". American Scientist, vol. 80 No. 6, November-December.

(56) References Cited

OTHER PUBLICATIONS

Klein, S., Aeschlimann, J.F., Appelbaum, M.A., Balsiger, D.F., Curtis, E.J., Foster, M Kalish, S.D., Lee, Ying-Da, Price, L.A. "Simulation D'Hypotheses Emises Par Propp et Levi-Strauss En Utilisant Un Systeme De Simulation Meta-Symbolique", Informatique et Sciences Humaines, No. 28, Mars 1976, pp. 66-133.

Hays D., Bozena Henisz-Dostert and Marjorie Rapp (editor). "Annotated Bibliography of Rand Publications in Computational Linguistics." Rand Memorandum RM-3894-3. 1965. pp. 1-5.

Klein, S., Oakley, J.D., Suurballe, D., Ziesemer, R.. "A Program for Generating Reports on the Status and History of Stochastically Modifiable Semantic Models of Arbitrary Universes", Technical Report #142, Nov. 1971.

Klein, S., Aeschlimann, J.F., Balsiger, D.F., Converse, S.L., Court, C., Foster, M., Lao, R., Oakley, J.D. Smith, J. "Automatic Novel Writing: A Status Report", Technical Report #186, Jul. 1973.

Meta-Symbolic Simulation System (MESSY) User Manual by Matthew A. Appelbaum with Forward: The History of MESSY by Sheldon Klein, Computer Sciences Technical Report #272, Apr. 26, 1976.

Klein, S., Aeschlimann, J.F., Appelbaum, M.A., Balsiger, D.F., Curtis, E.J., Foster, M., Kalish, S.D., Lee, Ying-Da, Price, L.A. "Simulation D'Hypotheses Emises Par Propp et Levi-Strauss En Utilisant Un Systeme De Simulation Meta-Symbolique", Informatique et Sciences Humaines, No. 28, Mars 1976, pp. 66-133.

Klein, S., "The Analogical Foundations of Creativity in Language, Culture & the Arts: the Upper Paleolithic to 2100CE", Language, Vision & Music Aug. 9-11, 1999, edited by Paul McKevitt et al., pp. 20-32.

"Lecture to the London Mathematical Society on Feb. 20, 1947." Alan M. Turing. Unpublished Manuscript.

\* cited by examiner

Fig. 1

| ¬ |   |
|---|---|
| F | T |
| T | F |
| U | U |
| D | D |

(Negation)

| ∧ | F | T | U | D |
|---|---|---|---|---|
| F | F | F | F | F |
| T | F | T | U | D |
| U | F | U | U | F |
| D | F | D | F | D |

(Conjunction)

| ∨ | F | T | U | D |
|---|---|---|---|---|
| F | F | T | U | D |
| T | T | T | T | T |
| U | U | T | U | T |
| D | D | T | T | D |

(Disjunction)

Logical Connectives

Fig. 3  Semantic Network

Diagram of the arrays (with size = N)
associated with each Semantic Node

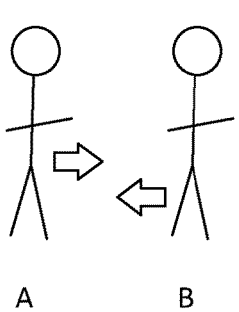
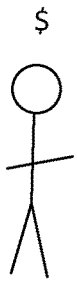
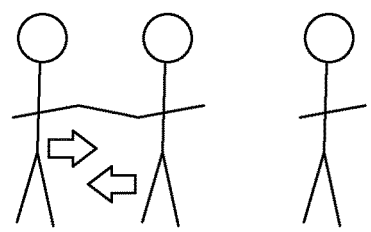
Fig. 6

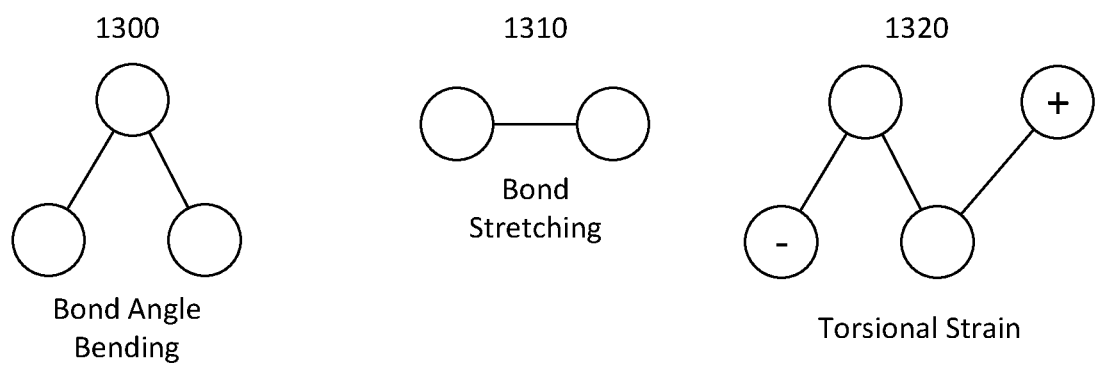
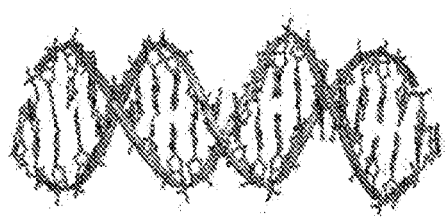
Fig. 9

METHODS AND SYSTEMS OF FOUR-VALUED GENOMIC SEQUENCING AND MACROMOLECULAR ANALYSIS

CROSS REFERENCE TO RELATED APPLICATIONS

This application is a continuation in part to U.S. patent application Ser. No. 14/016,518 filed on Sep. 3, 2013; Ser. No. 14/016,538 filed on Sep. 3, 2013, and Ser. No. 14/051,722 filed on Nov. 11, 2013, the contents of which are incorporated herein by reference.

COPYRIGHT AND TRADEMARK NOTICE

This application includes material which is subject or may be subject to copyright and/or trademark protection. The copyright and trademark owner(s) has no objection to the facsimile reproduction by any of the patent disclosure, as it appears in the Patent and Trademark Office files or records, but otherwise reserves all copyright and trademark rights whatsoever.

BACKGROUND OF THE INVENTION (1) Field of the Invention

The invention generally relates to computational tools for genomic sequencing and macromolecular analysis.

(2) Description of the Related Art

In the related art, various computational tools and machines for genome sequencing and analysis have been disclosed. But, the prior art lacks the efficiency of the presently disclosed embodiments.

BRIEF SUMMARY OF THE INVENTION

The present invention overcomes shortfalls in the related art by presenting an unobvious and unique combinations, configurations and use of methods, systems and means reducing the time and computational costs traditionally associated with testing, manipulation and analysis of data related to genomic sequencing and macromolecular analysis in computer architectures.

Disclosed embodiments overcome the shortfalls in the related art by presenting a notation that allows for the encoding of both syntactic and semantic information into a two bit vector notation associated with a semantic node in a semantic network. Disclosed embodiments also overcome shortfalls in the art by encoding the property each feature assumes in recursive predicate analysis using four-valued logic.

BRIEF DESCRIPTION OF THE DRAWINGS

FIG. 1 depicts a disclosed logic

FIG. 6 depicts computations of complex analogies

FIG. 9 depicts several properties that may be computed within a disclosed system These and other aspects of the present invention will become apparent upon reading the following detailed description in conjunction with the associated drawings.

DETAILED DESCRIPTION OF EMBODIMENTS OF THE INVENTION

Figure 2:
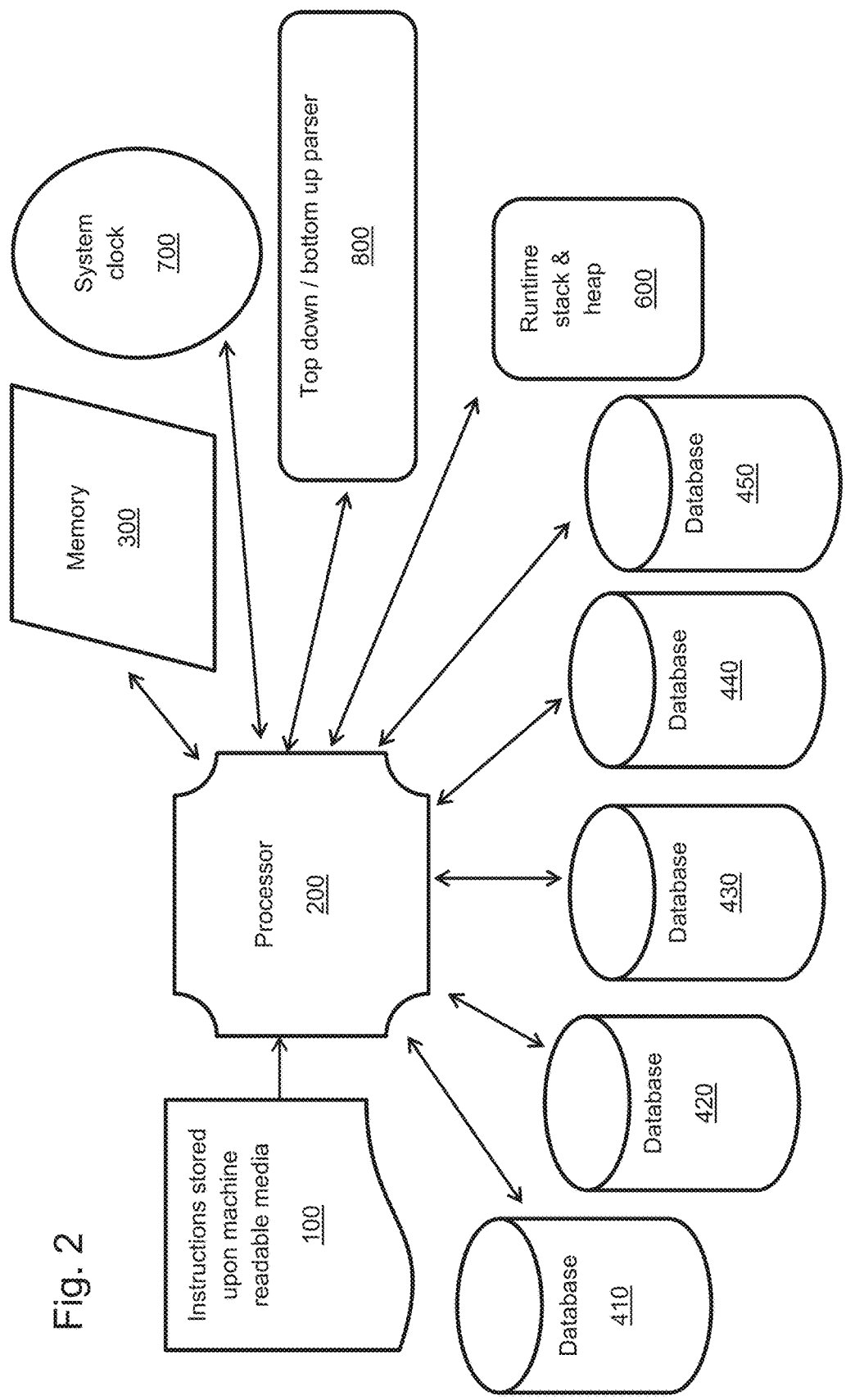
FIG. 2 depicts a machine implementation

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

All the above references and U.S. patents and applications are incorporated herein by reference. Aspects of the invention can be modified, if necessary, to employ the systems, functions and concepts of the various patents and applications described above to provide yet further embodiments of the invention.

Under the heading References is the academic literature specifically referenced in the application and is essential to the underlying invention.

Under the heading Further Reading is the academic literature relating to other academic work on this area of logic , added to assist patent searches and validate the mathematical claims of novelty. It is the mathematical properties of the four valued logics that have to be to correctly represent in implementations of the semantic network described Prof. by Sheldon Klein.

REFERENCES

Englemore, R. and Tony Morgan, (1988). Blackboard Systems. New York. Addisson Wesley Publishers.

Kleene, S., (1951) "Representation Of Events In Nerve Nets And Finite Automata". Rand Memorandum RM-704. December.

Kleene, S., (1952). Introduction to Metamathematics. North Holland.

Kleene, S. and Richard Vesley, (1965). The Foundations Of Intuitionistic Mathematics Especially In Relation To Recursive Functions. North-Holland.

Kleene, S., (1967). Mathematical Logic. John Wiley. New York.

Kleene, S., (1973)." Realizability: A Retrospective Survey". Cambridge Summer School in Mathematical Logic. Edited by Mathias, R. and H. Rogers. p.95-112.

Kleene,S., (1981). "The Theory of Recursive Functions, Approaching Its Centennial". Bulletin of the American Mathematical Society. Vol. 5, Number 1, July 1981.

Klein, S., Stephen Lieman and Gary Lindstrom, (1966). "DISEMINER: A Distributional Semantics Inference Maker". Carnegie Mellon University Tech Report #1719.

Klein, S., John Aeschlimann, Matthew Appelbaum, David Balsiger, Elizabeth Curtis, Mark Foster, David Kalish, Ying-Da Lee and Lynee Price.,(1976). FORWARD: The History of MESSY. University of Wisconsin Technical Report #272.

Klein, S., John Aeschlimann, Matthew Appelbaum, David Balsiger, Elizabeth Curtis, Mark Foster, David Kalish, Ying-Da Lee and Lynee Price. (1976) "Simulation D'Hypotheses Emises Par Propp & Levi-Strauss en Utilisant un Systeme de Simulation Meta-Symbolique". Informatique et Sciences Humaines. N. 28 Mars.

Klein, S.. (1981). "Culture, Mysticism and Social Structure and the Calculation of Behavior". University of Wisconsin Technical Report #462.

Klein, S. (1988). "Reply to S.D. Siemens' critique of S. Klein's 'Analogy and Mysticism and the Structure of Culture (Klein 1983)'. Current Anthropology 29. P. 478-483.

Klein, S. (2002). "The Analogical Foundations of Creativity in Language, Culture & the Arts: the Upper Paleolithic to 2100 CE". Language, Vision & Music, edited by Paul McKevitt, Mulvihill & Nuallin. John Benjamin, pp. 347-371.

Midmore, R. (2014).. "An interpretation of Sheldon Klein's Four Valued Analogical Transformational Operator". University of Wisconsin Tech Report #1801.

Searls, David. (1992). "The Linguistics of DNA". American Scientist, vol. 80 November-December Steedman, M.,(1992). "Categorial Grammar". University of Pennsylvania Department of Computer and Information Science Technical Report No. MS-CIS-92-52.

Yngve , V.,(1996). From Grammar to Science: New Foundations for General Linguistics. Amsterdam.

Zhurkin, V. and N. Ulyanov, A. Gorin and R. Jernigan. (1991). "Static and statistical bending of DNA evaluated by Monte Carlo simulations". Proceeding of the National Academy of Sciences US. vol.88 no. 16

Further Reading

Brouwer, E., (1981). Brouwer's Cambridge Lecture on Intuitionism. Edited by D. van Dalen.

Dubarle, D., (1977). Logos et Formalisation Du Langage. Paris. Dubarle, D., (1989). "Essai sur la generalisation naturelle de la logique usuelle (premier memoire)" Mathematiques et sciences humaines, vol.107. p. 17- 73.

Halton, J., (1968). "A Retrospective and Prospective Survey Of The Monte Carlo Method". University of Wisconin Computer Science Tech Report #13. February 1968.

Herdan, G. (1966). The Advanced Theory of Language as Choice or Chance. Spring-Verlag.

Lukasiewicz, J. (1955). Aristotle's Syllogistic From the Standpoint of Modern Formal Logic. 2nd edition. Oxford.

Piaget, J., (1952). "Essai sur les transformations des operations logiques. Les 256 operations ternaires de la logique bivalente". Paris Piaget, J., (1953). Logic and Psychology. Manchester University Press.

Reichenbach, H., (1949). The Theory of Probability. Los Angeles. (Proofed by Stephen Kleene) Troelstra, A.S., (1999)."From Constructivism to Computer Science". Theoretical Computer Science, num. 211, 1999 p. 233-252.

Turing, Alan, (1947). "Lecture To The London Mathematical Society on 20 Feb. 1947". Unpublished Manuscript. In Alan Turing: His work and Impact. Edited by S. Cooper and Jan Leeuwen. 2012.

Turing, Alan, (1954). "Solvable and Unsolvable Problems". Science News, no. 31, p. 7-23

REFERENCE NUMBERS 100 non transitory machine readable medium sometimes containing machine readable instructions
200 a general or specialized processor
300 memory, sometimes non volatile
410 database of one or more semantic networks
420 database of vector arrays
430 database of logical connectives
440 database of grammar phrase structure implementations
450 database of system reports
500 semantic network
510 objects
520 relations
600 runtime stack and heap
700 system clock
800 top down/bottom up parser
900 hash table of constructive primitive formulas
910 hash table of the functors and terms
920 properties that are immediately passed securable
921 general chart parser
922 solution state at time t
923 solution state at time t plus one
930 hash table of the lexicon (class)
940 symbol table
1000 depicts an analogical example using the four valued logic and reformulating the prior art of Sheldon Klein from his paper Culture, Mysticism and Social Structure and the Calculation of Behavior. Computer Sciences Technical Report #462 December 1981.
1010 depicts a continuing example of 1000.
1020 depicts a continuing example of 1000
1030 depicts a accompanying pictorial analogy of 1000
1040 depicts an accompanying pictorial analogy of 1010
1100 depicts a continuing analogical computation from 1000
1110 depicts a continuing analogical computation from 1000
1120 depicts a continuing analogical computation from 1000
1130 depicts a continuing pictorial computation from 1000
1140 depicts a continuing pictorial computation from 1000
1200 depicts a continuing analogical computation from 1000
1210 depicts a continuing analogical computation from 1000

1220 depicts a continuing pictorial computation from 1000

1230 depicts a continuing pictorial computation from 1000

1240 depicts a question mark which represents a complex analogy to have been computed 1300 depicts a bond angle bend 1310 depicts a bond stretch 1320 depicts a torsional strain 1340 depicts DNA Referring to FIG. 1, a diagram for the basic binary operators and negation, ignoring monotonic arguments for negation, for a four valued logic is described. These operators are used in proving the completeness for a family of logics. These logics can be derived from a variety of different arguments. From considerations of Boolean groupings on the truth values, a pre-ordering of the truth tables into a lattice structure, or from set theoretic and recursive definitions. All are constructed to preserve some of the primary axioms in classical logic. By modeling the recursive values the truth values assume explicitly in the semantic network simplifies the testing of conditionals and the quantification of variables. The undefined value, the default value for growth to the system, allows for the dynamic benign encoding into the network, a logic property attributable to many Kleene logics. The fourth property allows for the proper quantification and binding of variables for the elimination of the effects of the newer truth values for subsequent steps in the calculation. It also provides the possibility for the introduction of a constructively acceptable "tertium non datur" for decision procedures for modeling Markov processes into the logic.

By encoding properties with a specific bit into the bit vector the linear scaling may be maintained. This system is a departure from prior art in complier design for creating symbol tables, testing of features and aids extended stack compiler implementations.

In first column of FIG. 1, the logical not sign is shown as ¬, in the second column of FIG. 1 the AND operator is shown as ^, in the third column of FIG. 1 the OR operator is shown as V. The first column shows the values before application of the not operator. For example, in the first row of the first column, the value of F is shown before application of the not operator and T is shown as a result.

In the second column, a OR operator takes one value from the first column and one value from the first row and shows the result of the logical operator where the column value and row value intersect. In the third column a AND operator is applied in a similar manner as in the second column. For example, in the third column, at the first row and selecting the last element, at the first column in selecting the second element D and F are shown and result in a value of D.

Referring to FIG. 2, a machine implementation is shown using a machine readable, non-transitory media 100, the media 100 having machine readable instructions sent to a general or specialized processor 200. The processor 200 may be in communication with memory 300, a plurality of databases and other components, such as a network, user interfaces and other implements. The plurality of databases may include a database 410 of one or more semantic networks, such as the network system of FIG. 3, a database 420 of vector arrays the arrays may be associated with each semantic node or other network component, a database 430 of logical connectives, such as the connectives of FIG. 1, a database 440 of grammar phrase structure implementations, such as the and a database of other disclosed components FIG. 5 also depicts a system clock 700, top down/bottom up parser 800 and runtime stack and heap 600.

Figure 3:
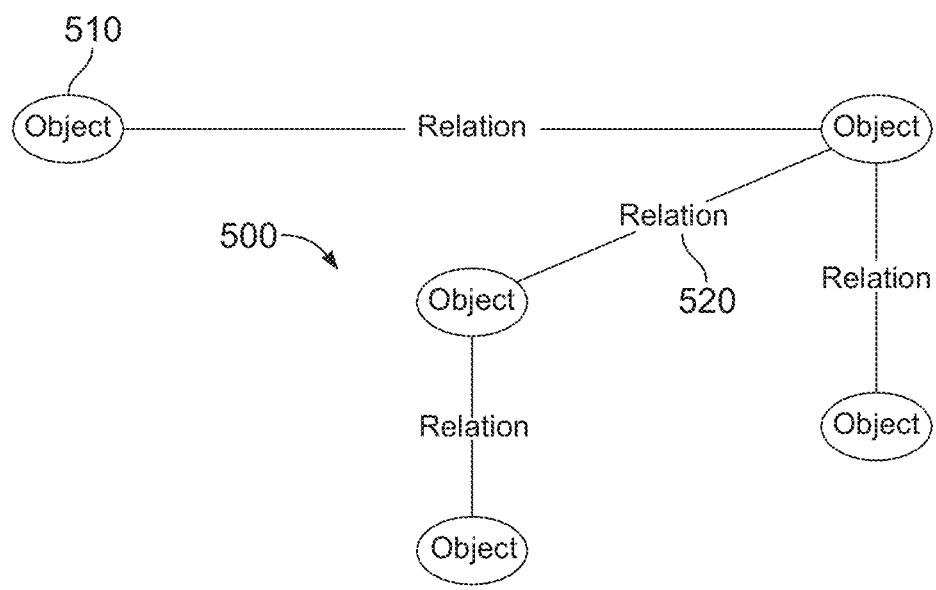
FIG. 3 depicts graphical representation of a semantic network

Referring to FIG. 3, a graphical representation of a semantic network 500 is shown with objects 510 and relations 520, with all objects and relations being nodes in memory or in a database.

Figure 4:
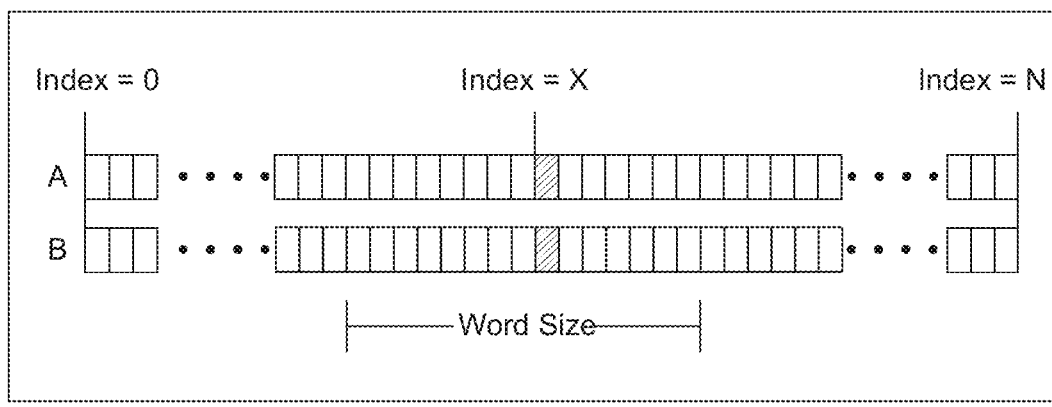
FIG. 4 depicts the assignment of a property to a particular index within array

FIG. 4 depicts a graphical representation of the two bit vector array associated with the semantic node in memory. FIG. 4 further shows the assignment of the truth value across the two arrays, with X being a specific index into the array. The word size in the figure is a consequence of word size limitations in computer architecture. This causes a chunking factor for implementations of the array.

Figure 5:
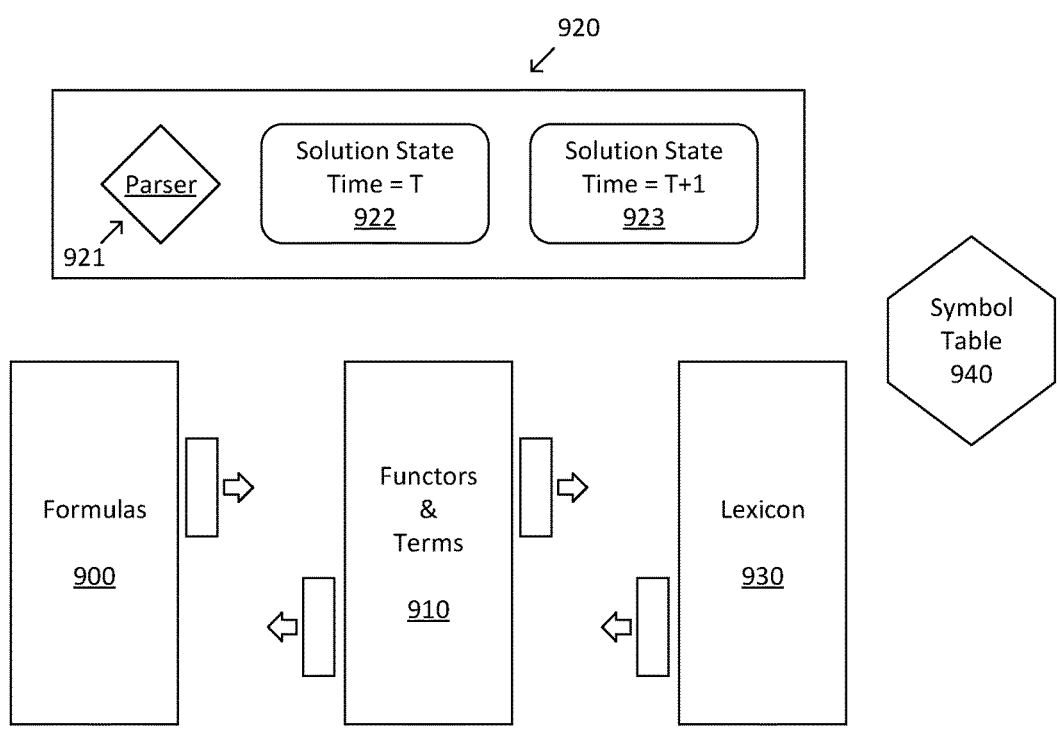
FIG. 5 depicts a disclosed general layout of principled data structures

FIG. 5 is a simple diagram depicting a general layout of the data structures assumed to be all contained in the same space of random access memory or RAM in a constructive formalization to highlight disclosed system diagnostics. 930 is a hash table of a lexicon for enforcing class membership. 910 is a hash table for functors and terms. 900 is a hash table for formulas. 920 is shared memory for a chart parser and a solution state of a computation controlling what is immediately securable in a simulation. 940 depicts a symbol has table responsible for mapping properties in their assignment in a bit vector.

FIG. 5 highlights the important logical divisions in constructive analysis which are important for systems analysis of the system in general and how it is using computer resources for specific algorithms in specific environments. Functors and terms are a logical term from Kleene's *The Foundations Of Intuitionistic Mathematics* and are equivalent to the use of object and relations in the writings of Klein. By restricting Klein's semantic triple to its 2-tuple subset one may model formulas consisting of Kleene's primitive recursive functions in the system. The notion of immediate securability is taken care of by the chart parser and its control of the solution state for the simulation. The system may be seen as allowing a timed memory access (i.e. massive sequential write from memory to the processes on the solution state (blackboard)) as the parser switches the blackboard from time T to time T+1. It's this timing by the parser with the system clock that allows for the determination of use of all system resources as this write may be given to a distributed system (i.e. network) and be seen as the timing of transmission in information theory for analysis of the system. The arrows and boxes represent the linkages (pointers) between specific entries that are related in the hash tables between the formulas (2-tuple & 3-tuple triples), terms/formulas (object/relations) and lexicon (class) for lookup (search).

Kleene's formulization is very restrictive and one may allow the loosening of logical standards to include general recursive formulas (allowing Klein's triple semantic notation in its fullest) as well as the notion of class which is taken care of by the lexicon in Klein's theories. Equating lambda definability and the notion of special realizability of Kleene with the notion of algorithm by Markov in *The Theory of Algorithms* will allow for a more colloquial presentation of the system. All that is needed in the diagram is to replace Lexicon with Markov's syllables, Objects/Relations with Markov's words, and formulas with Markov's notion of normal algorithms. His general rewrite system can then be assumed it's abilities in general pattern matching and replacement of strings in DNA sequences or strings more generally.

FIG. 6 is a diagram of a reformulation of a three valued analogical example given by Prof. Klein. It maps the value true to [1,1] and uses the strong equivalence operator for analogical relations. The exclusive OR is preferred so as to not make the system machine dependent and for the absence of the strong equivalence operator in major programming languages, use of the strong equivalence is shown since it is the preferred operator by logicians and one may interchange the four-valued strong equality operator with it's two-valued counterpart and use the notion of traditional equality when reviewing the logical literature.

The metamathematical values in FIG. 6 are True mapped to [1,1], False mapped to [0,1], Undefined [0,0], and Defined [1,0].

Figure 7:
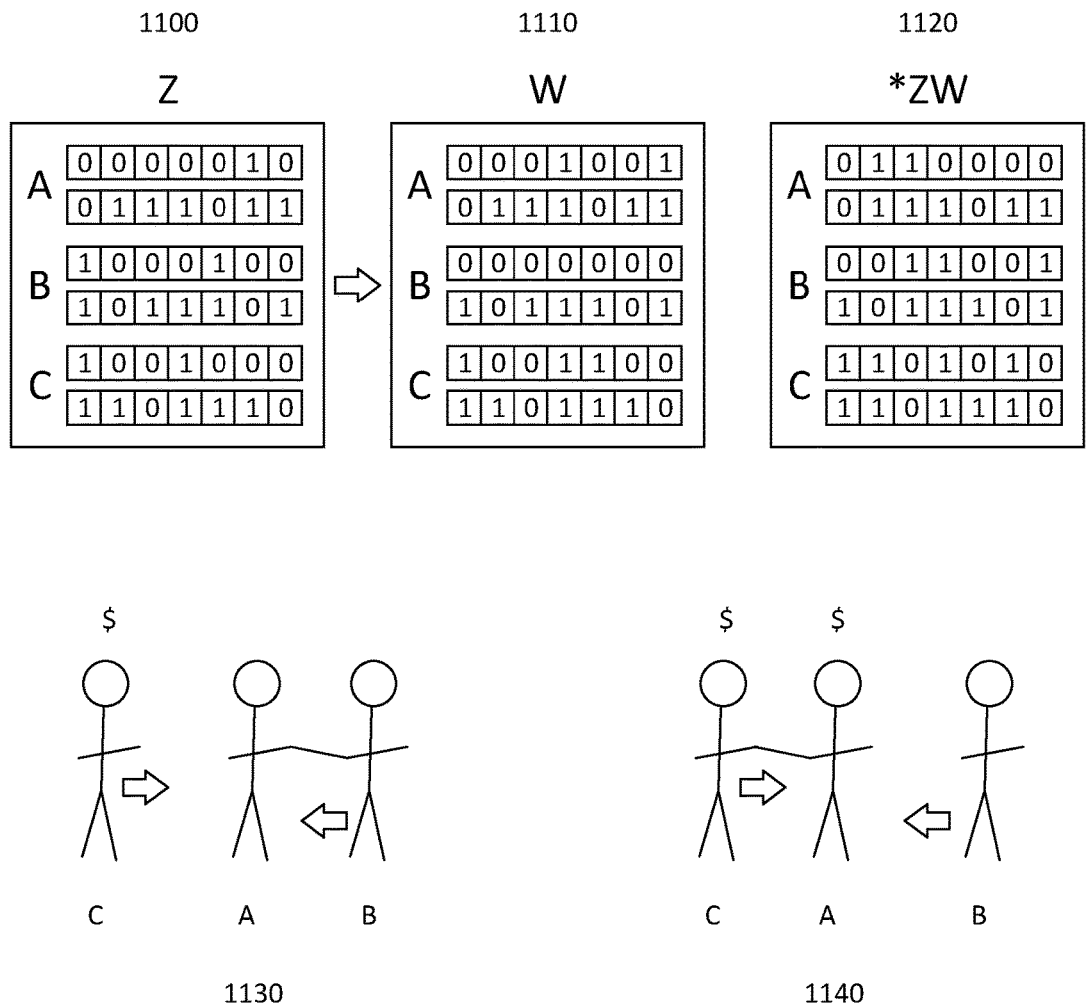
FIG. 7 is a continuation of FIG. 6

FIG. 7 is the continuation of 6

Figure 8:
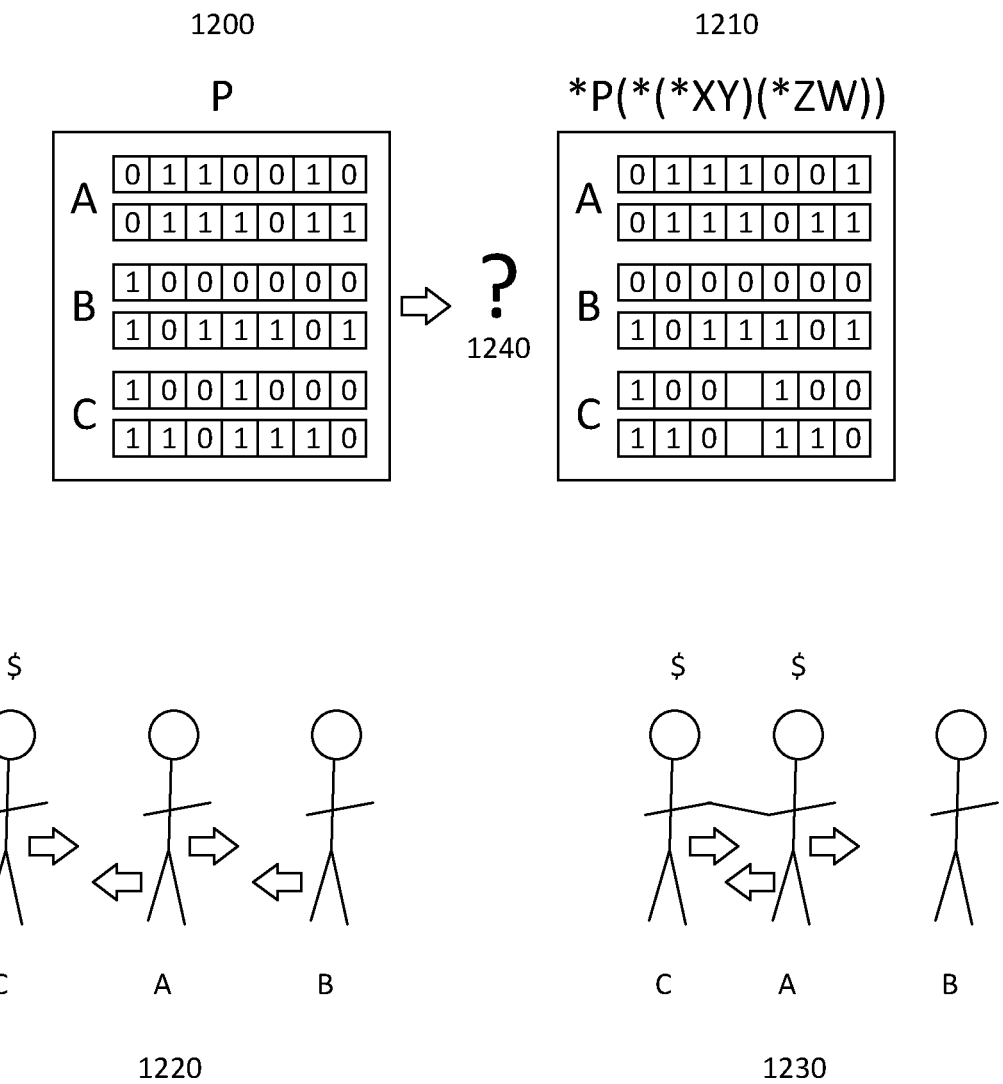
FIG. 8 is a continuation of FIG. 6

FIG. 8 is the continuation of 6

FIG. 9 is a diagram of some of the macromolecular properties being capable of being modelled in the system. 1310 is a diagram of bond stretching. 1300 is a diagram of angle bends. 1320 is a diagram of rotational or torsional stretching. 1340 depicts a DNA molecule.

These are some of the general molecular mechanical properties that are used in modeling, these properties may be interchanged with quantum mechanics but the computation time will increase significantly with this switch away from classical mechanics. Modeling according to the systems and methods disclosed herein can aid in the design of drugs, pharmaceutical research, genetically modified organisms and the detection of genetic sequences for gene therapy. The described four-valued parallelized simulation can combine a mixture of computer intensive techniques in DNA analysis and molecular crystallography.

These and other changes can be made to the invention in light of the above detailed description. In general, the terms used in the following claims, should not be construed to limit the invention to the specific embodiments disclosed in the specification, unless the above detailed description explicitly defines such terms. Accordingly, the actual scope of the invention encompasses the disclosed embodiments and all equivalent ways of practicing or implementing the invention under the claims.

While certain aspects of the invention are presented below in certain claim forms, the inventors contemplate the various aspects of the invention in any number of claim forms.

Disclosed embodiments include the following Items:

Item 1. A machine implemented method comprising a semantic network for genome sequencing and analysis, the method comprising:

using symbols comprising (F, T, U, D) to represent the values false, true, undefined, and defined, mapped into a two vector dynamic array; the values further mapped into indexes within the two vector dynamic arrays and stored as nodes within a semantic network for representing inputted genetic sequences;

for F, T, U, D, defined into set theory, such as { } for undefined, {T} for true, {F} for false, { } for undefined and {T, F} for defined, these values are interpreted as properties {P} for T and, {¬P} false, { } for undefined and {P, ¬P} for defined, which are the properties used for testing the conditionals and quantifying variables for successive recursive steps in the predicate calculus;

c) defining a logic with a negation, ignoring monotonic argumentations, with the following binary connectives: for the logical AND (^), NOT (¬); and logical OR (V) connectives as follows used to prove the completeness of the logics:

¬F is T
¬T is F
¬U is D
¬D is U;

d) for the ^ connective
^ FTUD
F FFFF
T FTUD
U FUUF
D FDF D;

e) for the V connective
V FTUD
F FTUD
T TTTT
U UTUT
D DTTD;

f) optimizing short term memory maximizing long term storage by the linear encoding of syntactic and semantic information into the semantic network;

g) in a parallel context optimizing short term memory to maximize long term storage becomes optimizing communication and memory between different knowledge sources (processes) and;

h) using defined and undefined to help separate asset classes in the simulation.

The method of item 1 further comprising using the use of a phrase structure rewrite rule associated with a node within the semantic network for the testing and passing of the rewrite rule.

The method of item 2 implementing a top/down, bottom/up parser capable of a plurality of syntactic parses of a grammar.

The method of item 3 using a system clock, runtime stack and heap, a processor, machine readable instructions contained on non-transitory media and a database of rewrite rules, a database of the semantic network and a database of syntactic and semantic information.

The system of item 4 implementing a top/down, bottom/up parser capable of a plurality of syntactic parses of a grammar to provide syntactic pattern matching abilities for modeling pattern matching for DNA sequences.

The system of item 5 implemented for dynamic modeling of DNA in Monte Carlo simulations, for the use of whole genomic sequences.

The system of item 5 using a specialized processor.

Item 8. A machine implemented method comprising a semantic network for macromolecular analysis, the method comprising:

using symbols comprising (F, T, U, D) to represent the values false, true, undefined, and defined, mapped into a two vector dynamic array; the values further mapped into indexes within the two vector dynamic arrays and stored as nodes within a semantic network for representing inputted macro molecular mechanics;

for F, T, U, D, defined into set theory,
such as { } for undefined, {T} for true, {F} for false, { } for undefined and {T, F} for defined, these values are interpreted as properties {P} for T and, {¬P} false, { } for undefined and {P, ¬P} for defined, which are the properties used for testing the conditionals and quantifying variables for successive recursive steps in the predicate calculus;

c) defining a logic with a negation, ignoring monotonic argumentations, with the following binary connectives: for the logical AND (^), NOT (¬); and logical OR (V) connectives as follows used to prove the completeness of the logics:

¬F is T
¬T is F
¬U is D
¬D is U;

d) for the ˆ connective
ˆ FTUD
F FFFF
T FTUD
U FUUF
D FDFD;
e) for the V connective
V FTUD
F FTUD
T TTTT
U UTUT
D DTTD;
f) optimizing short term memory maximizing long term storage by the linear encoding of syntactic and semantic information into the semantic network;
g) in a parallel context optimizing short term memory to maximize long term storage becomes optimizing communication and memory between different knowledge sources (processes) and;
h) using defined and undefined to help separate genetic types in the simulation.

Item 9. A system for the hybrid modeling of genetic sequences and macromolecular structures for chemical discoveries in key lock systems and induced fit systems the system comprising:

machine readable instructions stored upon a nonvolatile computer readable medium, a central processing unit, a runtime stack and heap, semantic network, top down/bottom up parser, a system clock, database with historical economic information;

the system using a Boolean encoding comprising (F, T, U, D) to represent the values false, true, undefined, and defined, mapped into a two vector dynamic array; the values further mapped into indexes within the two vector dynamic arrays and associated with nodes in a semantic network;

for {F, T, U, D} defined into set theory, such as { } for undefined, {T} for true, {F} for false, and {T,F} for defined, these values are interpreted as properties {P} for T, {¬P} for false, { } for undefined and {P, ¬P} for defined, which are the properties used for the testing of conditionals and quantifying of variables in the predicate calculus;

the system defining a logic with a negation with the following binary connectives: for the logical AND (ˆ), NOT (¬); and logical OR (V) connectives as follows used to prove the completeness of the logics:
¬F is T
¬T is F
¬U is D
¬D is U;
e) for the ˆ connective
ˆ FTUD
F FFFF
T FTUD
U FUUF
D FDF D;
f) for the V connective
V FTUD
F FTUD
T TTTT
U UTUT
D DTTD;
g) the system optimizing short term memory maximizing long term storage by the linear encoding of the information into the semantic network;
h) the system integrating memory in a parallel context to optimize communication and memory between different knowledge databases.

Item 10. The system of claim 9 further comprising using the use of a phrase structure rewrite rule associated with a node within the semantic network for the testing and passing of the rewrite rule, the word size of the system imposing a chunking factor in the testing of conditionals in theoretic time O(C).

Item 11. The system of item 9 further comprising a database of vector arrays, with each array associated with each semantic node, a database of the semantic network and a database of a grammar phrase structure implementations and a database of logical connectives.

Item 12. The system of item 9 implementing a top/down, bottom/up parser capable of a plurality of syntactic parses of a grammar to efficient model the growth of the statistical summation in the search space.

Item 13. The system of item 9 used for the dynamic macromolecular modeling of DNA in Monte Carlo simulations, with the physical properties of the DNA.

What is claimed is:

1. A machine implemented method of executing four-valued logic in a semantic network for genome sequencing and analysis, the method comprising:

defining a logic system having a NOT logical connective denoted as "¬," an AND logical connective denoted as "∧," and an OR logical connective denoted as "∨," wherein false values are represented with an "F" symbol, true values are represented by a "T" symbol, undefined values are represented by a "U" symbol, and defined values are represented by a "D" symbol, such that for a property P false values are in a set {¬P}, true values are in a set {P}, undefined values are in a set{ }, defined values are in a set {P, ¬P}, wherein said logic system is proven complete and w-consistent by a set of statements comprising:
¬F is T, ¬T is F, ¬U is D, ¬D is U;
F∧F is F, F∧T is F, F∧U is F, F∧D is F;
T∧F is F, T∧T is T, T∧U is U, T∧D is D;
U∧F is F, U∧T is U, U∧U is U, U∧D is F;
D∧F is F, D∧T is D, D∧U is F, D∧D is D;
F∨F is F, F∨T is T, F∨U is U, F∨D is D;
T∨F is T, T∨T is T, T∨U is T, T∨D is T;
U∨F is U, U∨T is T, U∨U is U, U∨D is T; and
D∨F is D, D∨T is T, D∨U is T, D∨D is D;

generating a semantic network representing digitally stored information, said semantic network comprising a plurality of object nodes representing inputted genetic sequences and a plurality of relationships between said plurality of object nodes, by:

providing a first vector and a second vector in digital memory for each of said plurality of object nodes, each of said first vector and said second vector being a dynamically allocated array having a plurality of index positions each with a size of one bit;

linearly encoding semantic information for an object node by storing two bits that together encode a false value, true value, undefined value, or defined value, a first bit of said two bits being stored at an index position within the first vector associated with the object node, and a second bit of said two bits being stored at the same index position within the second vector associated with the object node;

linearly encoding syntactic information associated with said plurality of relationships in said digital memory; and testing conditionals or quantifying variables in said semantic network during successive recursive steps in a predicate calculus using said logic system, the false values, true values, undefined values, and defined values in the semantic information associated with said plurality of object nodes, and the syntactic information associated with said plurality of relationships, wherein linear encoding of semantic information and said syntactic information optimizes short term memory, maximizes long term storage, and optimizes communication and memory between different knowledge sources or processes.

2. The method of claim 1, further comprising applying phrase structure rewrite rule on said plurality of object nodes in said semantic network.

3. The method of claim 2, further comprising implementing a top/down, bottom/up parser configured of a plurality of syntactic parses of a grammar.

4. The method of claim 3, wherein said top/down, bottom/up parsers is coupled with a system clock, a runtime stack and heap, a processor, machine readable instructions contained on non-transitory media, a database of rewrite rules, a database storing said semantic network, and a database storing said syntactic information and said semantic information.

5. The method of claim 4, wherein said plurality of syntactic parses of a grammar provides syntactic pattern matching abilities when modeling pattern matching for DNA sequences.

6. The method of claim 5, further comprising dynamic modeling of DNA in Monte Carlo simulations, for the use of whole genomic sequences.

7. The method of claim 5, wherein said processor is a specialized processor.

8. A machine implemented method of executing four-valued logic in a semantic network for macromolecular analysis, the method comprising:

defining a logic system having a NOT logical connective denoted as "⌐," an AND logical connective denoted as "∧," and an OR logical connective denoted as "∧," wherein false values are represented with an "F" symbol, true values are represented by a "T" symbol, undefined values are represented by a "U" symbol, and defined values are represented by a "D" symbol, such that for a property P false values are in a set {⌐P}, true values are in a set {P}, undefined values are in a set{ }, defined values are in a set {P, ⌐P}, wherein said logic system is proven complete and w-consistent by a set of statements comprising:
⌐F is T, ⌐T is F, ⌐U is D, ⌐D is U;
F∧F is F, F∧T is F, F∧U is F, F∧D is F;
T∧F is F, T∧T is T, T∧U is U, T∧D is D;
U∧F is F, U∧T is U, U∧U is U, U∧D is F;
D∧F is F, D∧T is D, D∧U is F, D∧∧D is D;
F∨F is F, F∨T is T, F∨U is U, F∨D is D;
T∨F is T, T∨T is T, T∨U is T, T∨D is T;
U∨F is U, U∨T is T, U∨U is U, U∨D is T; and
D∨F is D, D∨T is T, D∨U is T, D∨D is D;

generating a semantic network representing digitally stored information, said semantic network comprising a plurality of object nodes representing macro molecular mechanics and a plurality of relationships between said plurality of object nodes, by:
providing a first vector and a second vector in digital memory for each of said plurality of object nodes, each of said first vector and said second vector being a dynamically allocated array having a plurality of index positions each with a size of one bit;
linearly encoding semantic information for an object node by storing two bits that together encode a false value, true value, undefined value, or defined value, a first bit of said two bits being stored at an index position within the first vector associated with the object node, and a second bit of said two bits being stored at the same index position within the second vector associated with the object node;
linearly encoding syntactic information associated with said plurality of relationships in said digital memory; and testing conditionals or quantifying variables in said semantic network during successive recursive steps in a predicate calculus using said logic system, the false values, true values, undefined values, and defined values in the semantic information associated with said plurality of object nodes, and the syntactic information associated with said plurality of relationships, wherein linear encoding of said semantic information and said syntactic information optimizes short term memory, maximizes long term storage, and optimizes communication and memory between different knowledge sources or processes, and;

wherein defined values and undefined values represent different genetic types and molecular structures in said semantic network.

9. A system for the hybrid modeling of genetic sequences and macromolecular structures for chemical discoveries in key lock systems and induced fit systems, the system comprising:

a computing device comprising a central processing unit, a runtime stack and heap, a top down / bottom up parser, and a system clock;

a logic system defined in memory of said computing device, said logic system having a NOT logical connective denoted as "⌐," an AND logical connective denoted as "∧," and an OR logical connective denoted as "∨," wherein false values are represented with an "F" symbol, true values are represented by a "T" symbol, undefined values are represented by a "U" symbol, and defined values are represented by a "D" symbol, such that for a property P false values are in a set {⌐P}, true values are in a set {P}, undefined values are in a set { }, and defined values are in a set {P, ⌐P}, wherein said logic system is proven complete and w-consistent by a set of statements comprising:
⌐F is T, ⌐T is F, ⌐U is D, ⌐D is U;
F∧F is F, F∧T is F, F∧U is F, F∧D is F;
T∧F is F, T∧T is T, T∧U is U, T∧D is D;
U∧F is F, U∧T is U, U∧U is U, U∧D is F;
D∧F is F, D∧T is D, D∧U is F, D∧D is D;
F∨F is F, F∨T is T, F∨U is U, F∨D is D;
T∨F is T, T∨T is T, T∨U is T, T∨D is T;
U∨F is U, U∨T is T, U∨U is U, U∨D is T;
D∨F is D, D∨T is T, D∨U is T, D∨D is D; and a non-transitory computer readable medium storing machine readable instructions for causing said computing device to perform the steps of:

generating a semantic network representing digitally stored information, said semantic network comprising a plurality of object nodes representing genetic sequences and macromolecular structures and a plurality of relationships between said plurality of object nodes, by:
providing a first vector and a second vector in digital memory for each of said plurality of object nodes, each of said first vector and said second vector being a dynamically allocated array having a plurality of index positions each with a size of one bit;

linearly encoding semantic information for an object node by storing two bits that together encode a false value, true value, undefined value, or defined value, a first bit of said two bits being stored at an index position within the first vector associated with the object node, and a second bit of said two bits being stored at the same index position within the second vector associated with the object node;

linearly encoding syntactic information associated with said plurality of relationships in said digital memory; and testing of conditionals or quantifying variables in said semantic network during successive recursive steps in a predicate calculus using said logic system, the false values, true values, undefined values, and defined values in the semantic information associated with said plurality of object nodes, and the syntactic information associated with said plurality of relationships, wherein linear encoding of said semantic information and said syntactic information optimizes short term memory, maximizes long term storage, and optimizes communication and memory between different knowledge databases.

10. The system of claim 9, said machine readable instructions further comprising applying a phrase structure rewrite rule on said plurality of object nodes in said semantic network for testing and passing of the rewrite rule, a word size of the system imposing a chunking factor in a testing of conditionals in theoretic time O(C).

11. The system of claim 9, wherein said first vector and said second vector for each of said plurality of object nodes is stored in a database of vectors, said plurality of object nodes and said plurality of relationships is stored in a semantic network database, a plurality of grammar phrase structure implementations is stored in a grammar database, and logical connectives of said logic system are stored in a logical connectives database.

12. The system of claim 9, wherein said top/down, bottom/up parser is configured to perform a plurality of syntactic parses of a grammar to efficiently model the growth of a statistical summation in a search space.

13. The system of claim 9, wherein said machine readable instructions further comprise instructions for dynamic macromolecular modeling of DNA in Monte Carlo simulations using physical properties of the DNA.

* * * * *